(12) United States Patent
Sun et al.

(10) Patent No.: US 11,969,220 B2
(45) Date of Patent: Apr. 30, 2024

(54) VERIFICATION METHOD OF OSTEOTOMY GUIDE TOOL, VERIFICATION SYSTEM AND DETECTION ELEMENT

(71) Applicant: Suzhou MicroPort Orthobot Co., Ltd., Jiangsu (CN)

(72) Inventors: Teng Sun, Jiangsu (CN); Feng Sun, Jiangsu (CN); Hui Shao, Jiangsu (CN); Chao He, Jiangsu (CN); Pengfei Liu, Jiangsu (CN)

(73) Assignee: SUZHOU MICROPORT ORTHOBOT CO., LTD., Jiangsu (CN)

( * ) Notice: Subject to any disclaimer, the term of this patent is extended or adjusted under 35 U.S.C. 154(b) by 38 days.

(21) Appl. No.: 17/857,929

(22) Filed: Jul. 5, 2022

(65) Prior Publication Data
US 2022/0331010 A1 Oct. 20, 2022

Related U.S. Application Data

(62) Division of application No. 16/861,677, filed on Apr. 29, 2020, now Pat. No. 11,413,093.

(30) Foreign Application Priority Data

Nov. 22, 2019 (CN) .......................... 201911157719.5

(51) Int. Cl.
*A61B 34/10* (2016.01)
*A61B 17/17* (2006.01)
(Continued)

(52) U.S. Cl.
CPC .......... *A61B 34/10* (2016.02); *A61B 17/1764* (2013.01); *A61B 34/20* (2016.02);
(Continued)

(58) Field of Classification Search
CPC . A61B 17/154; A61B 17/1764; A61B 17/155; A61B 17/157; A61B 2034/102;
(Continued)

(56) References Cited

U.S. PATENT DOCUMENTS 8,483,434 B2 7/2013 Buehner et al.
2008/0319491 A1 12/2008 Schoenefeld
(Continued)

FOREIGN PATENT DOCUMENTS

| CN | 101267776 A | 9/2008 |
| CN | 101356418 A | 1/2009 |

(Continued)

*Primary Examiner* — Samuel S Hanna
(74) *Attorney, Agent, or Firm* — MUNCY, GEISSLER, OLDS & LOWE, PC

(57) ABSTRACT

A detection element and a verification system are disclosed. The detection element includes a detection end for contacting a feature portion of the osteotomy guide tool; and a positioning target connected to the detection end and configured to provide a pose parameter of the feature portion of the osteotomy guide tool in a coordinate system of a trackable element. With this configuration, the osteotomy guide tool can be verified to avoid deformation of the osteotomy guide tool during repeated use or transportation, affecting its positioning accuracy and affecting the operation.

8 Claims, 8 Drawing Sheets

(51) Int. Cl.
*A61B 34/20* (2016.01)
*A61B 34/30* (2016.01)
*A61B 17/00* (2006.01)
*A61B 34/00* (2016.01)

(52) U.S. Cl.
CPC .... *A61B 34/30* (2016.02); *A61B 2017/00199* (2013.01); *A61B 2034/2051* (2016.02); *A61B 2034/2055* (2016.02); *A61B 2034/743* (2016.02)

(58) Field of Classification Search
CPC .... A61B 2017/00199; A61B 2034/105; A61B 2034/108; A61B 2034/2051; A61B 2034/2055; A61B 2090/3983; A61B 34/10; A61B 34/20; A61B 34/30
See application file for complete search history.

(56) References Cited

U.S. PATENT DOCUMENTS

| | | |
|---|---|---|
| 2014/0206990 A1 | 7/2014 | Epstein et al. |
| 2015/0182292 A1 | 7/2015 | Hlasio |
| 2019/0053852 A1 | 2/2019 | Schoenefeld |
| 2021/0068845 A1* | 3/2021 | Schers ............... A61B 17/02 |

FOREIGN PATENT DOCUMENTS

| | | |
|---|---|---|
| CN | 101426453 A | 5/2009 |
| CN | 102258399 A | 11/2011 |
| CN | 103017702 A | 4/2013 |
| CN | 105813592 A | 7/2016 |
| CN | 107468350 A | 12/2017 |
| CN | 107920860 A | 4/2018 |
| CN | 108627129 A | 10/2018 |
| CN | 109171962 A | 1/2019 |
| CN | 109620348 A | 4/2019 |
| CN | 109998682 A | 7/2019 |
| CN | 110352042 A | 10/2019 |
| CN | 110811834 A | 2/2020 |
| EP | 2298215 A1 | 3/2011 |
| JP | 6578528 B1 | 9/2019 |
| WO | WO2018104523 A1 | 6/2018 |

* cited by examiner

US 11,969,220 B2

VERIFICATION METHOD OF OSTEOTOMY GUIDE TOOL, VERIFICATION SYSTEM AND DETECTION ELEMENT

CROSS-REFERENCE TO RELATED APPLICATIONS

This application is a continuation of U.S. patent application Ser. No. 16/861,677, filed Apr. 29, 2020, which in turn claims the priority of Chinese patent application number 201911157719.5, filed on Nov. 22, 2019, the entire contents of which are incorporated herein by reference.

TECHNICAL FIELD

The present invention relates to the field of robot-assisted surgical systems and methods, and in particular, to a verification system and a detection element.

BACKGROUND

In artificial joint replacement surgeries, various positioners, guides and other tools are used in an osteotomy process before installation of the artificial joint to ensure the accuracy of the osteotomy. Different approaches have been proposed to assist surgeons to achieve positioning of the osteotomy guide tools during total knee joint replacement (TKR) surgery. Generally, in the existing robot-assisted surgical system, an osteotomy guide tool is provided at the end of the robotic arm, and the robotic arm controls the guide motion of the osteotomy guide tool to realize the positioning of the osteotomy guide tool during the knee replacement surgery. During registration of the robotic arm, both the robotic arm system and the positioning system need to obtain the geometric center point of the osteotomy guide tool. Only when the geometric center point of the guide tool obtained by the robotic arm system and the geometric center point of the guide tool obtained by the positioning system are coincide or the same point, the conversion matrix obtained by the registration of the robotic arm can be correct. When the osteotomy guide tool is deformed, the positioning system cannot recognize the deformation, which will affect the positioning accuracy of the operation and thus affect the operation result.

SUMMARY OF THE INVENTION

In view of the above, an objective of the present disclosure is to provide a verification method of an osteotomy guide tool, a verification system and a detection element, to solve the problem that the existing robot-assisted surgical system cannot identify the deformation of the osteotomy guide tool.

In one aspect, the present disclosure provides a verification method of an osteotomy guide tool, including:
obtaining a pose parameter of a feature portion of an osteotomy guide tool in a coordinate system of a trackable element; and
comparing the obtained pose parameter of the feature portion of the osteotomy guide tool with a corresponding standard value to obtain an offset between the pose parameter of the feature portion of the osteotomy guide tool and the standard value;
wherein if the offset is greater than an expected value, the osteotomy guide tool is determined as deformed.

Optionally, in the verification method of an osteotomy guide tool, the feature portion includes a geometric center point of an osteotomy guide block of the osteotomy guide tool, and wherein the step of obtaining a pose parameter of a feature portion of an osteotomy guide tool in a coordinate system of a trackable element includes:
obtaining a plurality of pose parameters of a plurality of surfaces of the osteotomy guide block of the osteotomy guide tool in the coordinate system of the trackable element;
calculating an intermediate plane between every two opposite surfaces of the plurality surfaces according to the plurality of pose parameters of the plurality of surfaces; and
determining an intersection point defined by the intersecting intermediate planes as the geometric center point of the osteotomy guide block, and calculating a pose parameter of the geometric center point of the osteotomy guide block in the coordinate system of the trackable element.

Optionally, in the verification method of an osteotomy guide tool, the step of obtaining a plurality of pose parameters of a plurality of surfaces of the osteotomy guide block of the osteotomy guide tool in the coordinate system of the trackable element includes:
acquiring pose parameters of a plurality of feature points or feature lines on each surface of the osteotomy guide block by using a detection element; and
determining the pose parameter of each surface according to the pose parameters of the plurality of feature points or feature lines on the each surface.

Optionally, in the verification method of an osteotomy guide tool, in the acquired plurality of feature points on each surface, at least three feature points of the plurality of feature points on each surface are not collinear or the feature lines on each surface are curved lines.

Optionally, in the verification method of an osteotomy guide tool, the feature portion includes an inner surface of a guiding groove and/or a guiding hole of an osteotomy guide block of the osteotomy guide tool, wherein the step of obtaining a pose parameter of a feature portion of an osteotomy guide tool in a coordinate system of a trackable element includes:
obtaining a pose parameter of the inner surface of the guiding groove and/or the guiding hole of the osteotomy guide block in the coordinate system of the trackable element according to a detection element whose detection end is inserted into the guiding groove and/or the guiding hole of the osteotomy guide block.

Optionally, in the verification method of an osteotomy guide tool, the feature portion includes the guiding groove of the osteotomy guide block, and wherein the step of obtaining a pose parameter of a feature portion of an osteotomy guide tool in a coordinate system of a trackable element includes, after the detection end of the detection element is inserted into the guiding groove: acquiring an information about a sliding of the detection end of the detection element in the guiding groove along an extending direction of the guiding groove.

Optionally, in the verification method of an osteotomy guide tool, the step of acquiring an information about a sliding of the detection end of the detection element in the guiding groove along an extending direction of the guiding groove includes: acquiring an information about a sliding of the detection end of the detection element along each of two open ends of the guiding groove to obtain a pose parameter of the inner surface of the guiding groove corresponding to each of the two open ends.

Optionally, in the verification method of an osteotomy guide tool, a width of the detection end of the detection element matches with a width of the guiding groove, and wherein the step of acquiring an information about a sliding of the detection end of the detection element in the guiding groove along an extending direction of the guiding groove includes: acquiring an information about a single sliding of the detection end of the detection element along the extending direction of each guiding groove to obtain a pose parameter of the inner surface of the guiding groove.

Optionally, in the verification method of an osteotomy guide tool, the step of comparing the obtained pose parameter of the feature portion of the osteotomy guide tool with a corresponding standard value includes: determining whether pose parameters of the inner surface of the guiding groove corresponding to two open ends thereof are in a same plane; wherein if not, the guiding groove is determined as deformed; or if so, comparing the pose parameters of the inner surface of the guiding groove corresponding to the two open ends with a standard value of the guiding groove.

Optionally, in the verification method of an osteotomy guide tool, the osteotomy guide tool is configured to be disposed at an end of a robotic arm, wherein the feature portion includes a geometric center point of an osteotomy guide block of the osteotomy guide tool, and wherein the step of obtaining a pose parameter of a feature portion of an osteotomy guide tool in a coordinate system of a trackable element includes:

driving the osteotomy guide tool by the robotic arm to rotate around a preset geometric center point of the osteotomy guide block; and calculating a pose parameter of the geometric center point of the osteotomy guide block in the coordinate system of the trackable element based on a point cloud information formed by the trackable element connected to the osteotomy guide tool during rotation.

Optionally, in the verification method of an osteotomy guide tool, during driving the osteotomy guide tool by the robotic arm to rotate around the preset geometric center point of the osteotomy guide block, connection points between the robotic arm and the osteotomy guide tool are taken as movement points, wherein the movement points each follows a circular movement around a movement center in a movement plane, wherein an angle between: i) a movement line defined by connecting any one of the movement points and the preset geometric center point and ii) a center line defined by connecting the movement center and the preset geometric center point is not smaller than 30°.

In another aspect, the present disclosure provides a detection element for verifying an osteotomy guide tool, including:

a detection end for contacting a feature portion of the osteotomy guide tool; and a positioning target connected to the detection end and configured to provide a pose parameter of the feature portion of the osteotomy guide tool in a coordinate system of a trackable element.

Optionally, in the detection element, the detection end includes a sharp portion for abutting the feature portion of the osteotomy guide tool.

Optionally, in the detection element, the detection end includes a plunger having a width matching with a width of a guiding groove of an osteotomy guide block of the osteotomy guide tool, and wherein the plunger is configured to be inserted into the guiding groove.

Optionally, in the detection element, the detection end includes a sheet portion having a length matching with a length of a guiding groove of an osteotomy guide block of the osteotomy guide tool and/or a pin having an outer dimension matching with an inner dimension of a guiding hole of the osteotomy guide block of the osteotomy guide tool.

Optionally, in the detection element, the detection end is detachably connected to the positioning target.

In still another aspect, the present disclosure provides a verification system, including:

an osteotomy guide tool, including an osteotomy guide block and a target mounting portion connected with the osteotomy guide block;

a detection element for verifying the osteotomy guide tool, including: a detection end for contacting a feature portion of the osteotomy guide tool; and a positioning target connected to the detection end and configured to provide a pose parameter of the feature portion of the osteotomy guide tool in a coordinate system of a trackable element;

the trackable element provided on the target mounting portion;

a navigation device configured to communicate with the trackable element and the detection element, thereby obtaining a pose parameter of the trackable element and the detection element by the positioning target; and a control device in communication with the navigation device;

wherein the detection end of the detection element is configured to contact the feature portion of the osteotomy guide tool, wherein the control device is configured to obtain the pose parameter of the feature portion in the coordinate system of the trackable element by the navigation device and the detection element, and wherein if an offset between the obtained pose parameter and a corresponding standard value is greater than an expected value, the osteotomy guide tool is determined as deformed.

Optionally, in the verification system, the detection end of the detection element includes a sharp portion for abutting the feature portion of the osteotomy guide tool.

Optionally, in the verification system, the detection end of the detection element includes a plunger having a width matching with a width of a guiding groove of an osteotomy guide block of the osteotomy guide tool, and wherein the plunger is configured to be inserted into the guiding groove.

Optionally, in the verification system, the detection end of the detection element includes a sheet portion having a length matching with a length of a guiding groove of an osteotomy guide block of the osteotomy guide tool and/or a pin having an outer dimension matching with an inner dimension of a guiding hole of the osteotomy guide block of the osteotomy guide tool.

In summary, the verification method of the osteotomy guide tool, the verification system and the detection element provided in the present disclosure relate: first obtaining a pose parameter of a feature portion of an osteotomy guide tool in a coordinate system of a trackable element; then comparing the obtained pose parameter of the feature portion of the osteotomy guide tool with a corresponding standard value to obtain an offset between the pose parameter of the feature portion of the osteotomy guide tool and the standard value; if the offset is greater than an expected value, the osteotomy guide tool is determined as deformed. With this configuration, the osteotomy guide tool can be verified to avoid deformation of the osteotomy guide tool during repeated use or transportation, affecting its positioning accuracy and affecting the operation.

BRIEF DESCRIPTION OF DRAWINGS

The implementation method of the present disclosure and the features, properties, and advantages of the related embodiments will be described by referring to the following drawings, in which.

In these drawings.

Figure 1:
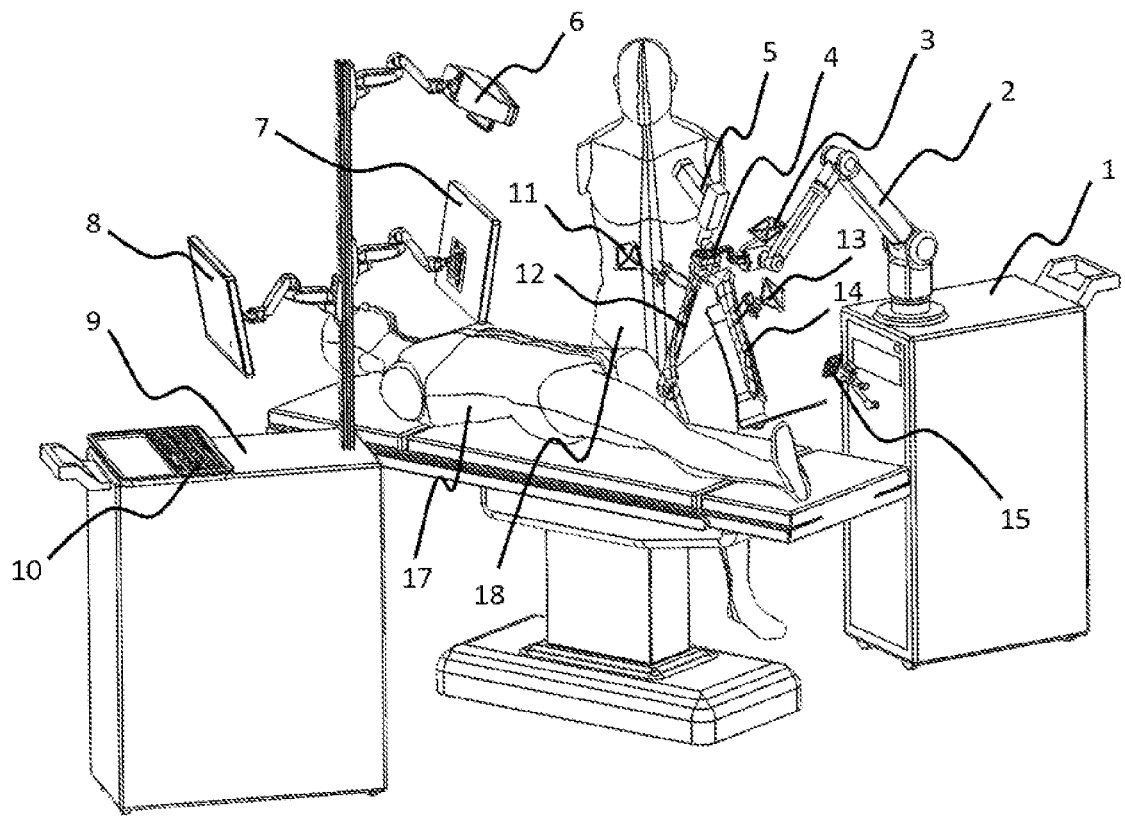
FIG. 1 is a schematic diagram of knee joint replacement using an orthopedic surgical system according to Embodiment 1 of the present disclosure.

1—surgical trolley; 2—robotic arm; 3—trackable element; 4—osteotomy guide tool; 5—swing saw; 6—NDI navigation device; 7—auxiliary display; 8—main display; 9—navigation trolley 10—keyboard; 11—femoral target; 12—femoral; 13—tibial target; 14—tibial; 15—basal target; 17—patient; 18—operator; 30—target mounting portion; 40—osteotomy guide block; 41—guiding groove; 42—guiding hole; 405—right leg pulley-osteotomy groove; 407, 411—0° guiding groove; 408, 410—45° guiding groove; 412—left leg pulley-osteotomy groove;

100—detection element; 101—detection end; 102—positioning target.

DETAILED DESCRIPTION OF EXEMPLARY EMBODIMENTS

The above and other objectives, features and advantages of the present disclosure will become more apparent from the following detailed description of the proposed surgical robot system, which is to be read in connection with FIGS. 1 to 14. Note that the figures are much simplified and may not be drawn to scale, and the sole purpose of them is to facilitate easy and clear explanation of the disclosed embodiments. In addition, the structure shown in the figures is often part of the actual structure. In particular, the figures show different emphases, and often adopt different proportions.

As used in the present disclosure, the singular forms "a", "an" and "the" include plural referents unless the content clearly dictates otherwise. As used in the present disclosure, the term "or" is generally used in its sense including "and/or" unless the content clearly dictates otherwise. As used in the present disclosure, the term "several" is generally used in its sense including "at least one" unless the content clearly indicates otherwise. As used in the present disclosure, the term "at least two" is generally used in its sense including "two or more" unless the content clearly indicates otherwise. In addition, the terms "first", "second" and "third" are used for descriptive purposes only, and cannot be understood as indicating or implying relative importance or implicitly indicating the number of technical features indicated. Therefore, the features defined as "first", "second" and "third" may explicitly or implicitly include one or at least two of the features.

The present disclosure is to provide a verification method of an osteotomy guide tool, a verification system and a detection element, to solve the problem that the existing robot-assisted surgical system cannot identify the deformation of the osteotomy guide tool.

The verification method of an osteotomy guide tool includes: obtaining a pose parameter of a feature portion of an osteotomy guide tool in a coordinate system of a trackable element; and comparing the obtained pose parameter of the feature portion of the osteotomy guide tool with a corresponding standard value to obtain an offset between the pose parameter of the feature portion of the osteotomy guide tool and the standard value; wherein if the offset is greater than an expected value, the osteotomy guide tool is determined as deformed.

With this configuration, the osteotomy guide tool can be verified to avoid inaccurate positioning caused by deformation of the osteotomy guide tool during repeated use or transportation, and thereby ensuring accuracy and safety of the operation.

The following description is made with reference to the drawings.

Embodiment 1

Figure 2:
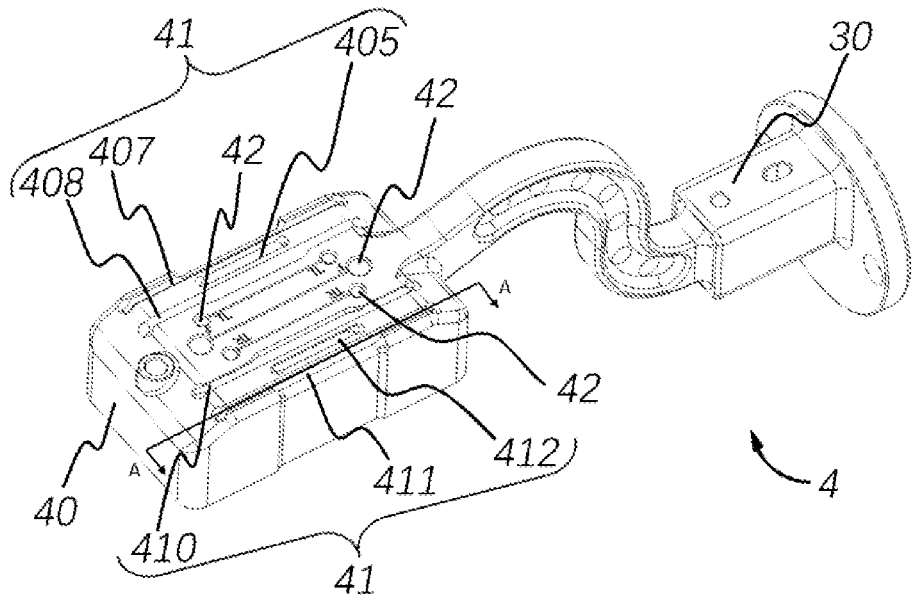
FIG. 2 is a schematic structural diagram of an osteotomy guide tool according to Embodiment 1 of the present disclosure.
Figure 3:
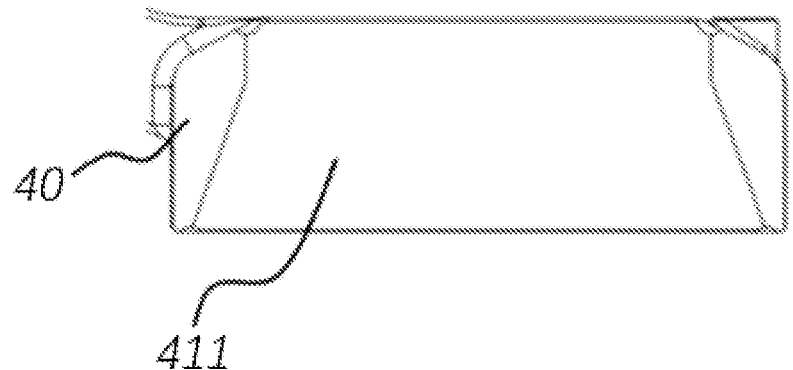
FIG. 3 is a cross-sectional view taken along line AA of the osteotomy guide tool shown in FIG. 2.
Figure 4:
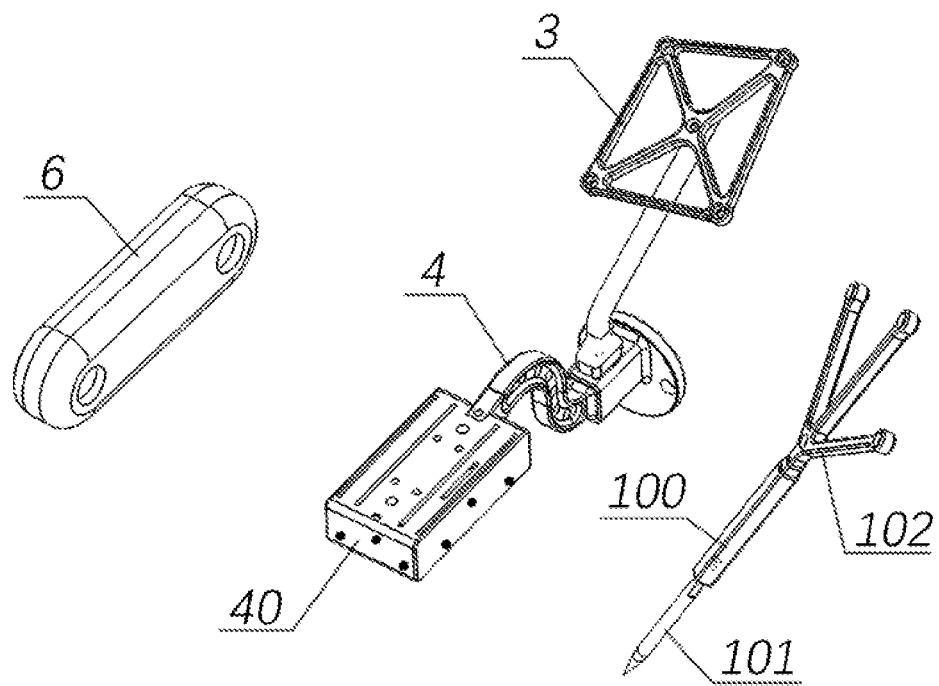
FIG. 4 is a schematic diagram of a verification system for an osteotomy guide tool according to a first example of Embodiment 1 of the present disclosure.
Figure 5:
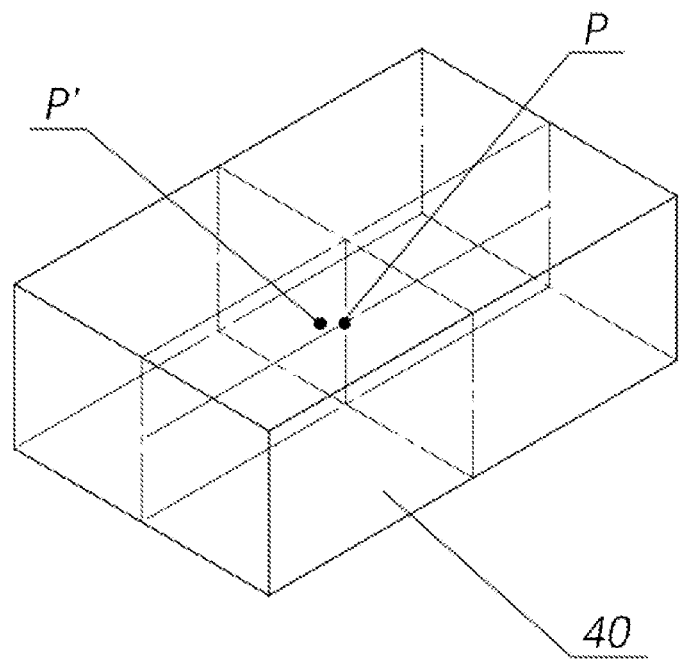
FIG. 5 is a schematic diagram of obtaining the geometric center point of an osteotomy guide block according to Embodiment 1 of the present disclosure.
Figure 6:
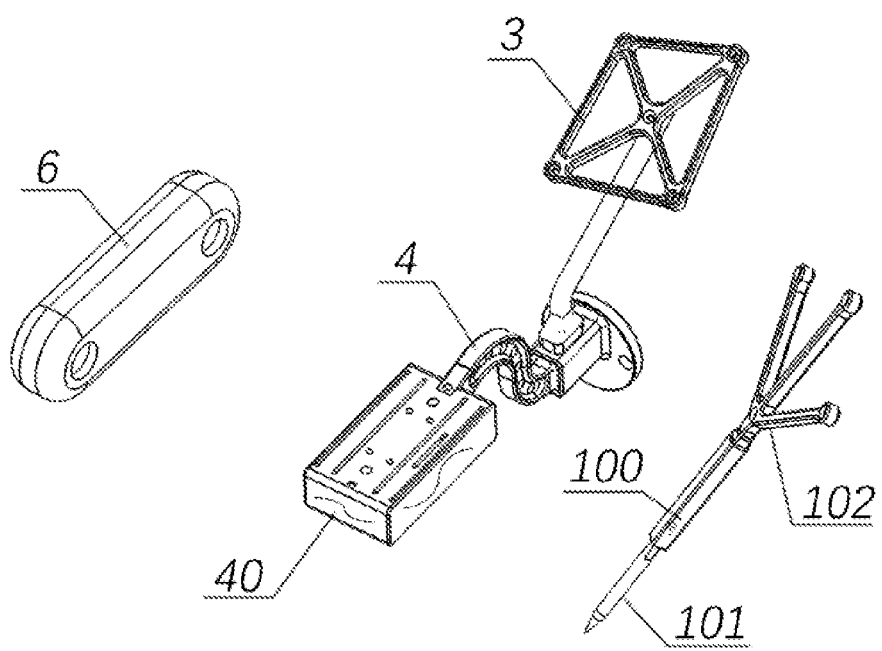
FIG. 6 is schematic diagram of a verification system for an osteotomy guide tool according to a second example of Embodiment 1 of the present disclosure.

Please refer to FIGS. 1 to 6, where FIG. 1 is a schematic diagram of knee joint replacement using an orthopedic surgical system according to Embodiment 1 of the present disclosure. FIG. 2 is a schematic structural diagram of an osteotomy guide tool according to Embodiment 1 of the present disclosure. FIG. 3 is a cross-sectional view taken along line AA of the osteotomy guide tool shown in FIG. 2. FIG. 4 is a schematic diagram of a verification system for an osteotomy guide tool according to a first example of Embodiment 1 of the present disclosure. FIG. 5 is a schematic diagram of obtaining the geometric center point of an osteotomy guide block according to Embodiment 1 of the present disclosure. FIG. 6 is schematic diagram of a verification system for an osteotomy guide tool according to a second example of Embodiment 1 of the present disclosure.

Embodiment 1 of the present disclosure provides an orthopedic surgical system. FIG. 1 is a schematic diagram of knee joint replacement using the orthopedic surgical system. However, the orthopedic surgical system of the present disclosure has no particular limitation on the application environment and can also be applied to other orthopedic surgeries. In the following description, an orthopedic surgical system is described using knee replacement as an example, but it should not be taken as a limitation of the present disclosure.

As shown in FIG. 1, the orthopedic surgical system includes a control device, a navigation device, a robotic arm 2 and an osteotomy guide tool 4. The control device is configured as a computer which is equipped with a controller, a main display 8 and a keyboard 10, and more preferably the computer is further equipped with an auxiliary display 7. In this embodiment, the contents displayed on the auxiliary display 7 and the contents displayed on the main display 8 are the same, for example, both are used to display osteotomy position images. The navigation device is an electromagnetic positioning navigation device, an optical positioning navigation device, or an electromagnetic positioning navigation device. In some embodiments, the navigation device is an optical positioning navigation device. Compared with other navigation methods, the measurement accuracy of the optical positioning navigation is higher, which can effectively improve the positioning accuracy of the osteotomy guide tool. In the following description, the optical positioning navigation device is taken as an example for description, but it is not limited herein.

The navigation device specifically includes a navigation marker and a tracker 6. The navigation marker includes a basal target 15 and a trackable element 3. The basal target 15 is fixed, for example, the basal target 15 is fixed on the surgical trolley 1 such that a base coordinate system (also referred to as a basal target coordinate system) is established. The trackable element 3 is mounted on the osteotomy guide tool 4 to track the position of the osteotomy guide tool 4. The osteotomy guide tool 4 is mounted at the end of the robotic arm 2 so that the osteotomy guide tool 4 is supported by the robotic arm 2 and the spatial position and the posture of the osteotomy guide tool 4 are adjusted by the robotic arm 2.

In practice, the tracker 6 is configured to capture the signal (preferably an optical signal) reflected by the trackable element 3 and record the position of the trackable element 3 (that is, the position and the posture of the trackable element under the base coordinate system). Then the instruction stored in the controller controls the movement of the robotic arm 2 according to the current position and the desired position of the trackable element. The robotic arm 2 drives the osteotomy guide tool 4 and the trackable element 3 to move, until the trackable element 3 is moved to the desired position. The expected position of the trackable element 3 corresponds to the desired position of the osteotomy guide tool 4.

Therefore, the application of the orthopedic surgical system can realize the automatic positioning of the osteotomy guide tool 4, and the trackable element 3 tracks and feeds back the real-time pose of the osteotomy guide tool 4 during the operation. The adjustment of the position and pose of the osteotomy guide tool is achieved by controlling the movement of the robotic arm. This not only ensures a high positioning accuracy of the osteotomy guide tool 4, but also prevents secondary injury to the human body, as the osteotomy guide tool 4 is supported by the robotic arm 2 and need not be fixed on the human body.

Generally, the orthopedic surgical system further includes a surgical trolley 1 and a navigation trolley 9. The control device and a part of the navigation device are mounted on the navigation trolley 9, for example, the controller is mounted inside the navigation trolley 9, and the keyboard 10 is placed outside the navigation trolley 9 for operation. The main display 8, the auxiliary display 7 and the tracker 6 are all mounted on a bracket, the bracket is vertically fixed on the navigation trolley 9, and the robotic arm 2 is mounted on the surgical trolley 1. The use of the surgical trolley 1 and the navigation trolley 9 eases the entire surgical operation. In some embodiments, the controller is mounted in the surgical trolley 1.

When performing knee joint replacement surgery, the use of the orthopedic surgical system of this embodiment generally includes the following operations:

first, moving the surgical trolley 1 and the navigation trolley 9 to appropriate positions next to the hospital bed;

then, providing the navigation markers (the navigation markers also include femoral target 11 and tibial target 13), the osteotomy guide tool 4 and other relevant components (such as sterile bags);

after that, the surgeon 18 imports the CT/MR scan model of the bone of the patient 17 into the computer for preoperative planning to obtain an osteotomy scheme. The osteotomy scheme includes, for example, the osteotomy scheme coordinates, the model of the prosthesis, and the installation orientation of the prosthesis. Specifically, based on the patient knee image data obtained from CT/MR scans, an osteotomy scheme is created based on the three-dimensional digital model of the knee joint, so that the surgeon can perform preoperative evaluation according to the osteotomy scheme. Specifically, the osteotomy scheme is determined based on the three-dimensional digital model of the knee joint in combination with size specifications of the obtained prosthesis and installation position of the osteotomy plate. The osteotomy scheme is finally output in the form of a surgical report, which records a series of reference data such as the coordinates of the osteotomy plane, the amount of osteotomy, the angle of the osteotomy, the size of the prosthesis, the installation position of the prosthesis, and the surgical aids/assisting tools, especially a series of theoretical explanations, such as the reason for selecting the osteotomy angle are provided as a reference for the surgeon. The three-dimensional digital model of the knee joint can be displayed on the main display 8 and the surgeon can enter surgical parameters via the keyboard 10 for preoperative planning.

After the preoperative evaluation, the surgeon 18 then uses a target pen or a pole with tracking elements to mark the guiding features on the patient's femur and tibia (that is, the surgeon marks multiple femoral anatomical guiding features on the patient's femoral entity and multiple tibial anatomical guiding features on the patient's tibial entity). The navigation device takes the basal target 15 as a reference, records the positions of all guiding features on the patient's tibia 14 and femur 12, and sends the position information of all guiding features to the controller, and then the controller obtains the actual orientations of the femur 12 and the tibia 14 by means of the feature matching algorithm, and corresponds the orientations to those of the femur 12 and the tibia 14 shown in the CT/MR images.

Subsequently, the actual orientations of the femur and the tibia are linked to the corresponding targets mounted on the femur and the tibia by the navigation device, so that the femoral target 11 and the tibia target 13 can track the current position of the bone in real time. The relative position between the target and the bone is fixed, the bone movement will not affect the surgical effect.

Further, the coordinate of the osteotomy scheme planned before the operation is sent to the robotic arm 2 by the navigation device. After the robotic arm 2 locates the osteotomy scheme through the trackable element 3 and moves to the predetermined position, the robotic arm 2 is in the holding state (that is, the robotic arm 2 does not move). After that, the surgeon/operator can use the surgical tool 5 such as a pendulum saw or an electric drill to perform osteotomy and/or drilling operations by the osteotomy guide tool 4. After the osteotomy and drilling operations are completed, the surgeon can install the prosthesis and perform other surgical operations.

In this embodiment, the navigation marker further includes a femur target 11 and a tibial target 13. The femoral target 11 is configured to locate/track the spatial position and the posture of the femur 12, and the tibial target 13 is configured to locate/track the spatial position and the posture of the tibia 14. As mentioned before, the trackable element 3 is mounted on the osteotomy guide tool 4, but in other embodiments, the trackable element 3 is alternatively mounted on the end joint of the robotic arm 2.

Based on the above orthopedic surgical system, robot-assisted surgery can be realized to assist the surgeon/operator locate the desired position for osteotomy and perform the osteotomy. Please refer to FIG. 2 and FIG. 3, which illustrate an osteotomy guide tool 4 provided in this embodiment. The osteotomy guide tool 4 includes an osteotomy guide block 40 and a target mounting portion 30. The target mounting portion 30 is configured for connection of the trackable element 3. The osteotomy guide block 40 is provided with guiding features. The guiding features include a guiding groove 41 or a guiding hole 42, or a combination of a guiding groove 41 and a guiding hole 42. That is, the guiding features on the osteotomy guide block 40 may be one or more combinations of the guiding groove 41 and the guiding hole 42, thereby providing one or more guides for osteotomy of knee replacement, specifically providing guides for osteotomy and drilling operations of the distal femur, the front of the femur, the back of the femur, the oblique of the front of the femur, the oblique of the back of the femur, the pulley groove, the femoral prosthesis mounting hole, the tibial plateau, and the tibial keel treatment locating hole, so that the same osteotomy guide tool can perform multiple operations of osteotomy and drilling. In practice, the position of the osteotomy guide tool 4 is represented by the position of the trackable element 3. It is also necessary to calibrate the posture mapping/corresponding relationship between the trackable element 3 and the osteotomy guide tool 4 in advance, such as according to the position information of the guiding feature relative to the center point of the osteotomy guide block 40 and the coordinate information (or the pose parameter) of the center point of the osteotomy guide block 40 in the coordinate system of the trackable element, obtaining the pose parameter (including position and the posture) of the guiding feature in the coordinate system of the trackable element, thereby forming a pose-parameter mapping relationship between the guiding feature and the trackable element 3.

In order to increase the scope of the prosthesis applicable to the osteotomy guide tool of the present disclosure, as shown in FIG. 2, the guiding groove 41 on the osteotomy guide block 40 is provided with 0° guiding grooves (407 and 411) and 45° guiding grooves (408 and 410), right leg-pulley osteotomy groove 405 and left leg-pulley osteotomy groove 412. When an osteotomy performed to the front of the femur, the oblique of the front of the femur, the back of the femur, and the oblique of the back of the femur, it is enough for the translation of the osteotomy guide block 40 to use the corresponding guiding groove to complete these osteotomy operations. Thus the trackable element 3 on the osteotomy guide block 40 will not cause/generate a large pose change, thereby reducing the transmission error of the robotic arm 2 and the target position tracking error, and improving the positioning accuracy. The shape of the guiding groove 41 is preferably a horn. FIG. 3 illustrates a cross section of the 0° guiding groove 411 along its extending direction. As can be seen, the two open ends (the upper and lower ends in the figure) of the 0° guiding groove 411 are different in size, the 0° guiding groove 411 has a shape of a horn as a whole, so as to increase the swing range of a surgical tool such as a pendulum saw in the guiding groove, so as to be compatible with osteotomy operations of more types of prostheses.

As mentioned above, since the orthopedic surgical system needs to be positioned based on the pose parameters of the feature portions on the osteotomy guide tool 4 for surgical operation, once the feature portions on the osteotomy guide tool 4 are deformed, in the orthopedic surgical system, the positioning accuracy will be affected because the failure of recognition of deformation of the feature portion on the osteotomy guide tool 4. Thus, this embodiment provides a verification method of an osteotomy guide tool which includes:

Step S1: obtaining a pose parameter of a feature portion of an osteotomy guide tool 4 in a coordinate system of a trackable element;

Step S2: comparing the obtained pose parameter of the feature portion of the osteotomy guide tool 4 with a corresponding standard value to obtain an offset between the pose parameter of the feature portion of the osteotomy guide tool 4 and the standard value; wherein if the offset is greater than an expected value, the osteotomy guide tool 4 is determined as deformed. Verifying of the pose parameters of the feature portions of the osteotomy guide tool 4 can avoid the deformation of the osteotomy guide tool 4 during repeated use or transportation, which affects its positioning accuracy and affects the operation.

Based on the above description, this embodiment provides a detection element 100 for verifying an osteotomy guide tool 4. The detection element 100 includes: a detection end 101 and a positioning target 102, the detection end 101 is used to contact with the feature portion of the osteotomy guide tool 4, the positioning target 102 and the detection end 101 is connected to provide pose parameters of the feature portion of the osteotomy guide tool in the coordinate system of the trackable element. The positioning target 102 may be an optical reflector for tracking and positioning of the navigation device 6, and the navigation device 6 sends the positioning information to the control device. The control device calculates a pose parameter of the feature portion in the coordinate system of the trackable element, if the offset between the pose parameter of the feature portion and the standard value is greater than an expected value, then the osteotomy guide tool 4 is determined as deformed. Preferably, the detection end 101 includes a sharp portion for abutting the feature portion of the osteotomy guide tool 4.

Preferably, the feature portion includes a geometric center point P of the osteotomy guide block 40 of the osteotomy guide tool 4, the step S1 includes:

Step SA1: obtaining a plurality of pose parameters of a plurality of surfaces of the osteotomy guide block 40 of the osteotomy guide tool 4 in the coordinate system of the trackable element;

Step SA2: calculating an intermediate plane between every two opposite surfaces of the plurality surfaces according to the plurality of pose parameters of the plurality of surfaces; and Step SA3: determining an intersection point defined by the intersecting intermediate planes as the geometric center point P of the osteotomy guide block 40, and calculating a pose parameter of the geometric center point P of the osteotomy guide block 40 in the coordinate system of the trackable element.

Please refer to FIG. 4, in the first example of this embodiment, the step SA1 includes: acquiring pose parameters of a plurality of feature points or feature lines on each surface of the osteotomy guide block 40 by using a detection element 100; and determining the pose parameter of each surface according to the pose parameters of the plurality of feature points or feature lines on each surface.

Specifically, in step SA1, using the sharp portion of the detection end 101 of the detection element 100 to acquire a plurality of feature points on each surface of the osteotomy guide tool 4, during the process of acquiring the feature points by the detection element 100, the navigation device 6 detects the trackable element 3 and sends the detected information to the control device. The control device calculates the pose parameter of the feature point in the coordinate system of the trackable element based on the detected information. Therefore, the pose parameter of the surface of the osteotomy guide block 40 in the navigation system is $Rt_W^A$, the pose parameter of the trackable element 3 in the navigation system is $Rt_W^B$, thus, the pose parameter $Rt_B^A = Rt_W^A - Rt_W^B$ of the surface of the osteotomy guide block 40 in the coordinate system of the trackable element can be obtained by the coordinate change.

Preferably, in the acquired plurality of feature points on each surface, at least three feature points of the plurality of feature points on each surface are not collinear. Generally, a plane can be determined by three non-collinear feature points, so in step SA1, it is preferable to obtain three feature points to determine a surface of the osteotomy guide block 40. Of course, those skilled in the art can select more feature points according to the actual needs, and there will be some redundant feature points in the more feature points, which can further improve the accuracy of the calculated surface.

Please refer to FIG. 5, in step SA2, the intermediate plane between every two opposite surfaces of the plurality surfaces is calculated according to the plurality of pose parameters of the plurality of surfaces of the osteotomy guide block 40 measured in step SA1. Since the pose parameters of all surfaces of the osteotomy guide block 40 are obtained, an intermediate plane can be calculated for every two opposing surfaces. Taking the osteotomy guide block 40 as an example of a cuboid, three intermediate planes can be obtained from six surfaces. Further, in step SA3, the intersection point of the three intermediate planes is defined as the geometric center point P of the osteotomy guide block 40. Of course, the osteotomy guide block 40 is not limited to a cuboid, and those skilled in the art can implement the determination of the geometric center point P of the osteotomy guide block 40 of other shapes according to the above descriptions. Since the transformation relationship of the pose parameter of the surface of the osteotomy guide block 40 in the coordinate system of the trackable element has been determined in the previous step SA1, the pose parameter of the geometric center point P in the coordinate system of the trackable element can also be easily obtained.

Further, in step S2, the standard value is the pose parameter of the expected center point P' of the osteotomy guide block 40 determined by a three-coordinate calibration instrument in the coordinate system of the trackable element. That is, the standard value is the expected center point P' without any deformation of the osteotomy guide block 40, which can be determined by the three-coordinate calibration instrument at the factory or obtained from the design value of the osteotomy guide tool 40. The expected value can be set according to the actual needs. If the offset is greater than the expected value, it means that the deformation of the osteotomy guide block 40 is large, which can no longer meet the accuracy requirements of the operation, the osteotomy guide tool 4 is determined as deformed, and the operator can replace or perform other treatments on the deformed osteotomy guide tool 4 according to the actual situation. Further, if the offset is not greater than the expected value, it means that the deformation of the osteotomy guide tool 4 is small, which can satisfy the accuracy of the operation, the operator can further choose whether to update the standard value to the pose parameter of the feature portion of the osteotomy guide tool 4 actually obtained in step S1, so as to perform the surgical operation more accurately later.

Please refer to FIG. 6, in the second example of this embodiment, the step SA1 includes: obtaining the pose parameters of the feature lines on each surface of the osteotomy guide block 40 by using a detection element 100 respectively; determining the pose parameter of each surface according to the pose parameters of the plurality of feature lines on each surface. In some embodiments, the feature lines acquired on each surface are curved lines. The curve line may have, for example, an "S" shape or the like. In practice, the sharp portion of the detection end 101 of the detection element 100 can be slide in an S shape on each surface of the osteotomy guide tool 4. Since the feature line is a curve line, a unique plane can be determined, so in step SA1, a surface of the osteotomy guide block 40 can be determined. Of course, those skilled in the art can select other types of feature lines according to the actual needs, such as polylines. The remaining method steps of the second example of this embodiment and the first example of this embodiment can refer to the above description.

In the above method, by obtaining the pose parameter of the surface of the osteotomy guide block 40, the pose parameter of the geometric center point of the osteotomy guide block 40 can be calculated. Furthermore, the calculated pose parameter of the geometric center point is compared with a standard value and an offset is obtained, wherein if the offset is greater than the expected value, the osteotomy guide tool is determined as deformed. With this configuration, the osteotomy guide tool can be verified to avoid deformation of the osteotomy guide tool during repeated use or transportation, affecting its positioning accuracy and affecting the operation.

Embodiment 2

Figure 7:
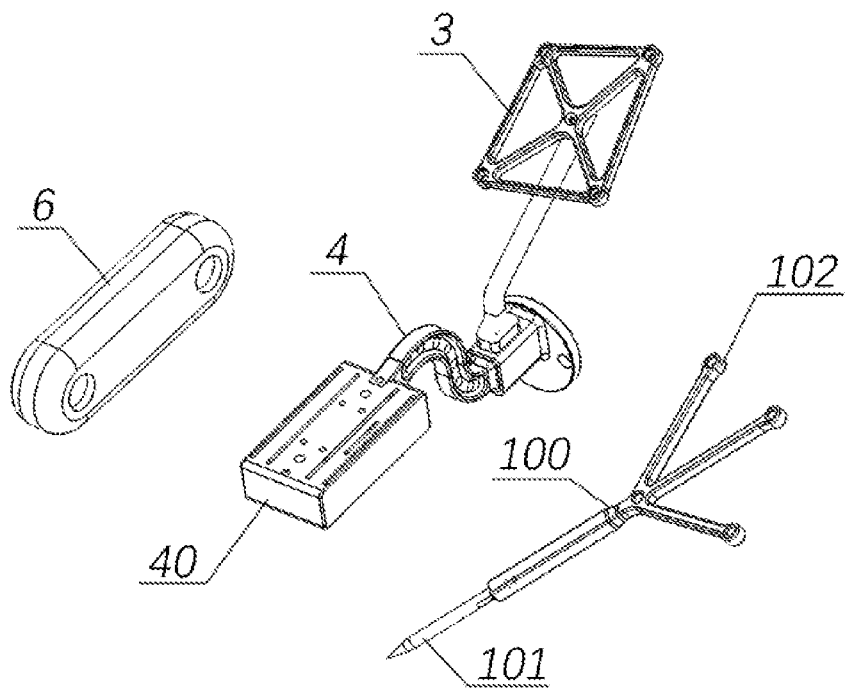
FIG. 7 is schematic diagram of a verification system for an osteotomy guide tool according to a first example of Embodiment 2 of the present disclosure.
Figure 8:
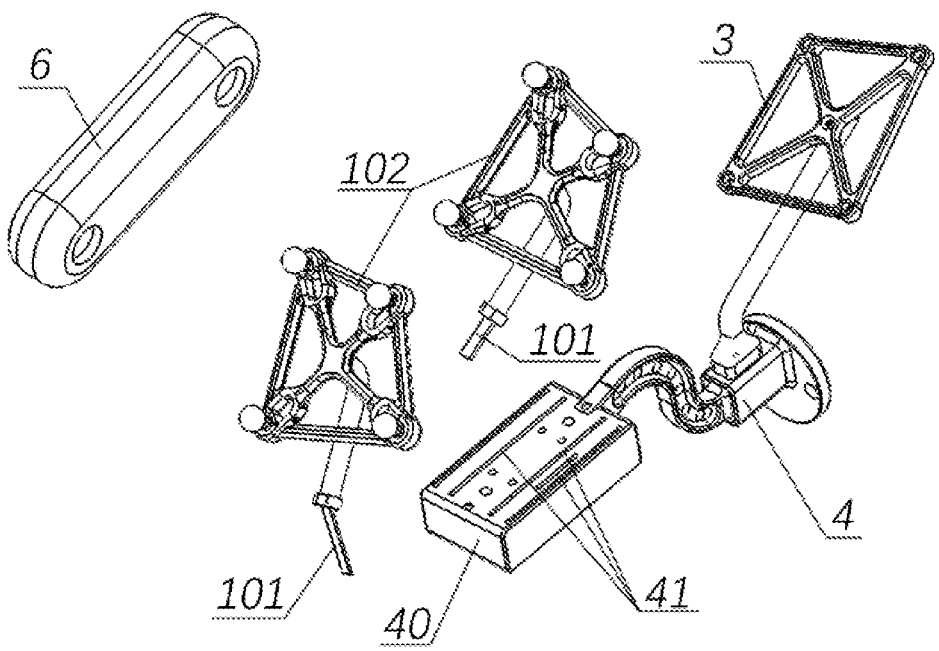
FIG. 8 is schematic diagram of another verification system for an osteotomy guide tool according to a second example of Embodiment 2 of the present disclosure.
Figure 9:
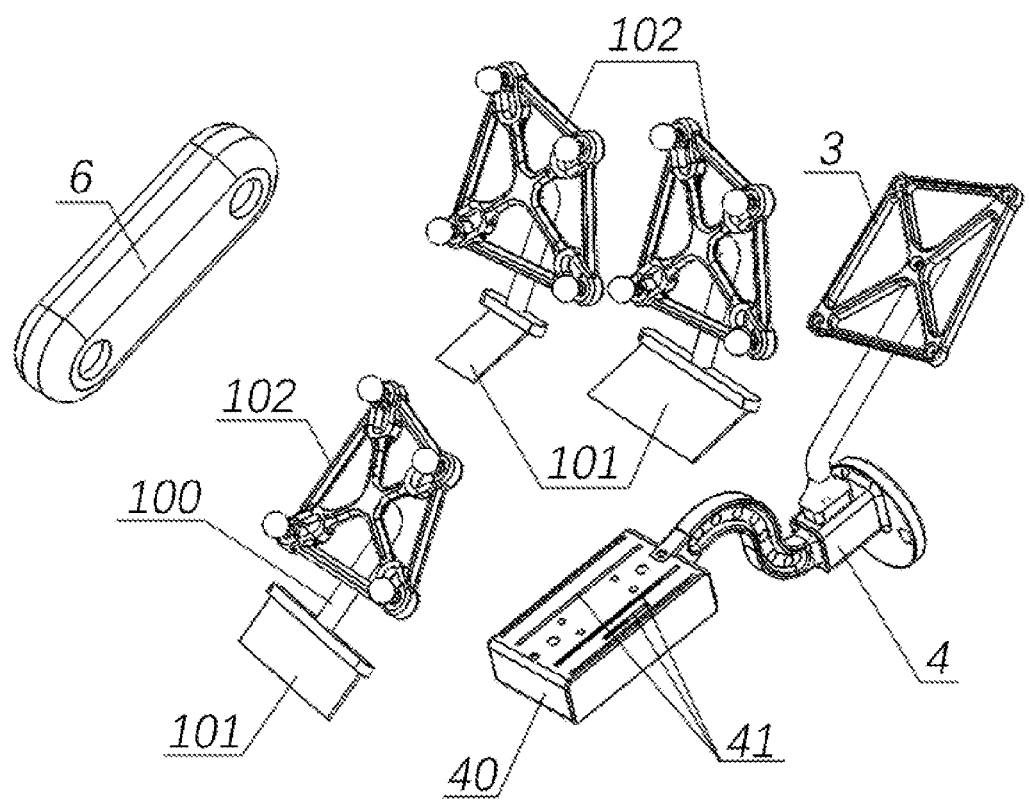
FIG. 9 is schematic diagram of still another verification system for an osteotomy guide tool according to a third example of Embodiment 2 of the present disclosure.
Figure 10:
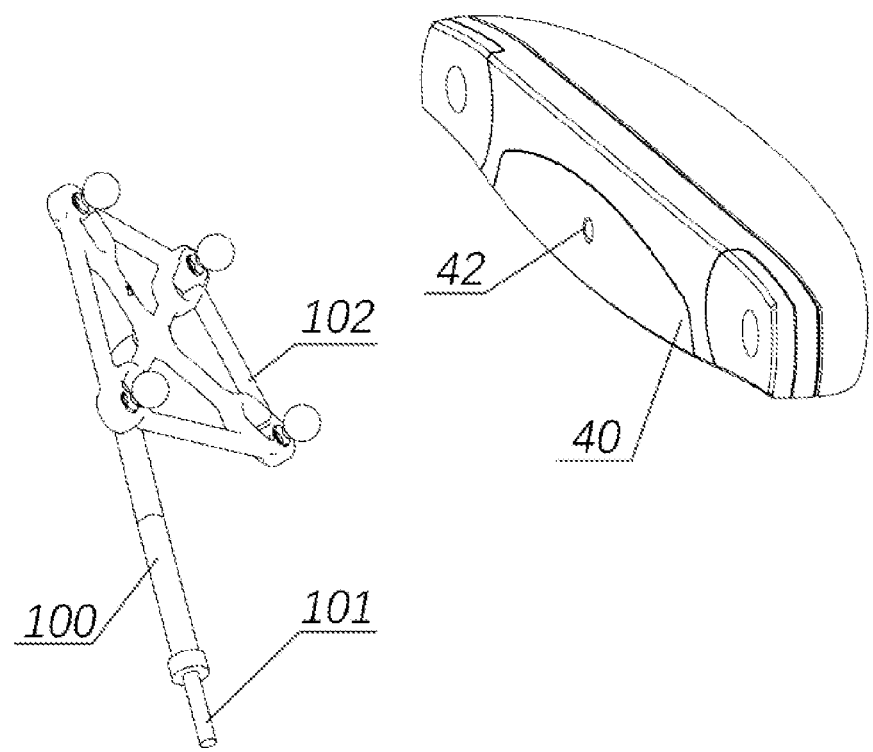
FIG. 10 is schematic diagram of the verification system for an osteotomy guide tool according to a fourth example of Embodiment 2 of the present disclosure.
Figure 11:
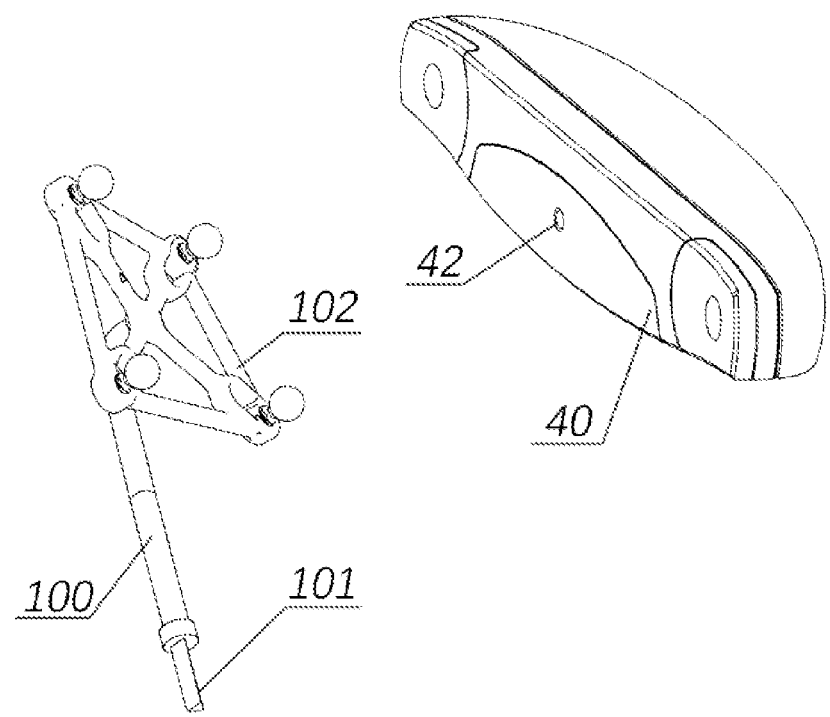
FIG. 11 is schematic diagram of the verification system for an osteotomy guide tool according to a fifth example of Embodiment 2 of the present disclosure.
Figure 12:
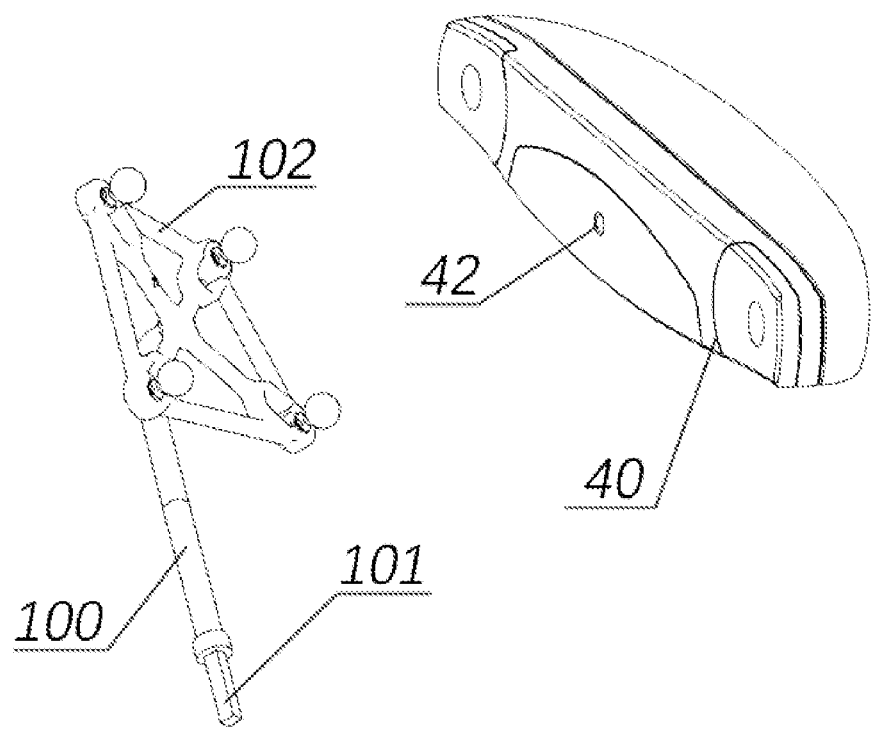
FIG. 12 is schematic diagram of the verification system for an osteotomy guide tool according to a sixth example of Embodiment 2 of the present disclosure.
Figure 13:
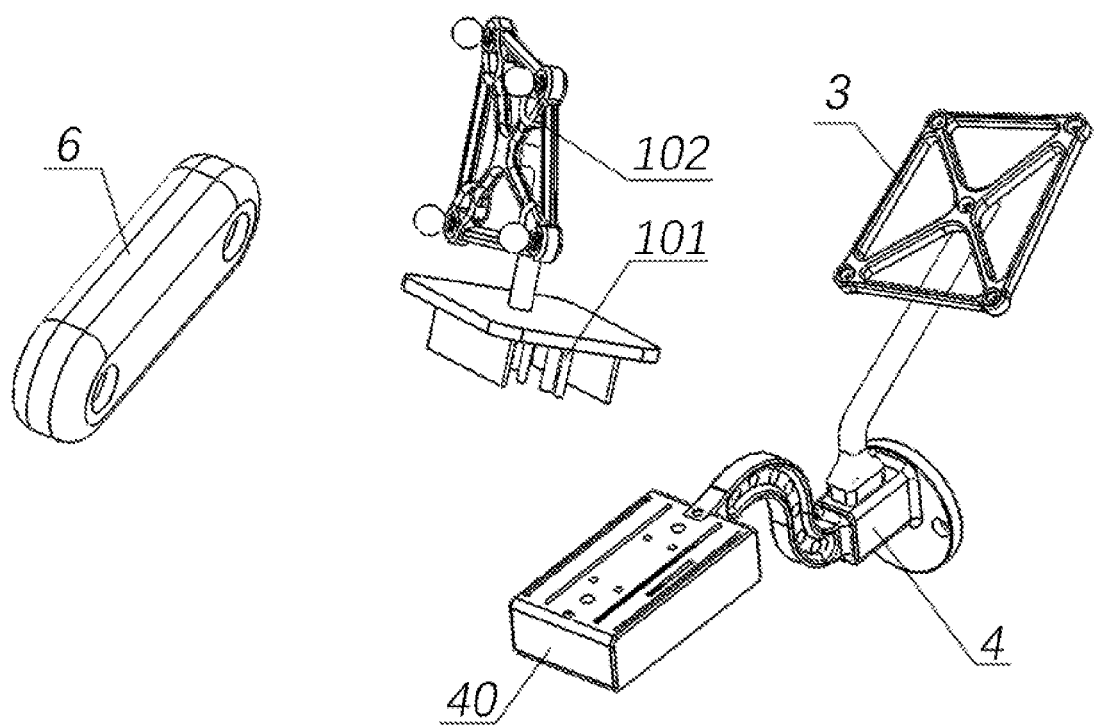
FIG. 13 is a schematic diagram of the verification system for an osteotomy guide tool according to a seventh example of Embodiment 2 of the present disclosure.

Please refer to FIGS. 7 to 13, wherein FIG. 7 is schematic diagram of a verification system for an osteotomy guide tool according to a first example of Embodiment 2 of the present disclosure. FIG. 8 is schematic diagram of another verification system for an osteotomy guide tool according to a second example of Embodiment 2 of the present disclosure. FIG. 9 is schematic diagram of still another verification system for an osteotomy guide tool according to a third example of Embodiment 2 of the present disclosure. FIG. 10 is schematic diagram of the verification system for an osteotomy guide tool according to a fourth example of Embodiment 2 of the present disclosure. FIG. 11 is schematic diagram of the verification system for an osteotomy guide tool according to a fifth example of Embodiment 2 of the present disclosure. FIG. 12 is schematic diagram of the verification system for an osteotomy guide tool according to a sixth example of Embodiment 2 of the present disclosure. FIG. 13 is a schematic diagram of the verification system for an osteotomy guide tool according to a seventh example of Embodiment 2 of the present disclosure.

The verification method of the osteotomy guide tool, the verification system and the detection element provided by the second embodiment of the present disclosure are basically the same as the verification method of the osteotomy guide tool, the verification system and the detection element provided by the first embodiment of the present disclosure. The same part will not be described, the following only describes the differences.

In this embodiment, the feature portion includes an inner surface of a guiding groove and/or a guiding hole of an osteotomy guide block 40 of the osteotomy guide tool 4. The step S1 includes: obtaining a pose parameter of the inner surface of the guiding groove 41 and/or the guiding hole 42 of the osteotomy guide block 40 in the coordinate system of the trackable element according to a detection element 100 whose detection end is inserted into the guiding groove 41 and/or the guiding hole 42 of the osteotomy guide block 40. Specifically, the step S1 includes:

Step SB1: inserting the detection end 101 of the detection element 100 into the guiding groove 41 and/or the guiding hole 42 of the osteotomy guide block 40;

Step SB2: obtaining a pose parameter of the inner surface of the guiding groove 41 and/or the guiding hole 42 of the osteotomy guide block 40 in the coordinate system of the trackable element according to the detection element 100.

Please refer to FIG. 7, in some embodiments, the feature portion includes the guiding groove 41 of the osteotomy guide block 40. After the detection element 100 is inserted into the guiding groove 41 in step SB1, the step S1 further includes: acquiring a sliding information of the detection end 101 of the detection element 100 when the detection element 100 slides in the guiding groove 41 along an extending direction of the guiding groove 41.

In the first example of this embodiment, the detection end 101 of the detection element 100 includes a sharp portion. As shown in FIG. 7, the sharp portion is a cone, and the size of the end of the sharp portion connected to the positioning target 102 is preferably larger than the size of the open end of the guiding groove 41. With this configuration, the sharp tip of the sharp portion can extend into the open end of the guiding groove 41, and the rest of the detection element 100 is stuck outside the open end of the guiding groove 41. The sharp portion of the detection end 101 is placed at the open end of the guiding groove 41, and then the detection end 101 slides in the guiding groove 41 along the extending direction of the guiding groove 41. The navigation device 6 can obtain the pose parameter of the open end of the guiding groove 41 by the positioning target 102. If the open end of the guiding groove 41 is distorted or deformed, it can be detected by the sliding of the detection element 100. In practice, each guiding groove 41 includes two open ends, so in practice it is necessary to obtain an information about a single sliding of the detection end 101 of the detection element 100 along the extending direction of each guiding groove 41 to obtain the pose parameter of the inner surface of each guiding groove 41 at the two open ends, respectively. In an embodiment, the osteotomy guide block 40 includes six guiding grooves 41. Each guiding groove 41 penetrates two opposite surfaces of the osteotomy guide block 40. So, it needs to respectively detect the twelve open ends of the six guiding grooves 41. Optionally, after the detection element 100 slides along the open ends on the same side of all the guiding grooves 41 and then slides along the open ends on the other side of all the guiding grooves 41. Optionally, in other embodiment, the detection element 100 verifies every two opposite open ends of each guiding groove 41 in pairs according to a preset sequence, or acquires the pose parameters of the open ends of all guiding grooves 41 with a single sliding. Then each corresponding guiding groove 41 is identified according to the feature point classification of all pose parameters.

Further, it is determined in sequence whether the pose parameters of the opposite two open ends of each guiding groove 41 are in the same plane. If the pose parameters of the two open ends of one guiding groove 41 are not in the same plane, it means that the corresponding guiding groove 41 is seriously deformed, which prompts/informs the operator that the osteotomy guide tool 4 has deformed. And if the pose parameters of the opposite two open ends of each guiding groove 41 are in the same plane, and then the pose parameters of the open end of each guiding groove 41 are further compared with corresponding standard values. It should be understood that the standard value corresponding to the pose parameter of the open end of the guiding groove 41 should be the design value preset by the expected pose parameter of the open end of the guiding groove 41, such as the design value preset at the factory. If the offset obtained by comparing the pose parameter of the open end of the guiding groove 41 with the corresponding standard value is greater than the expected value, it means that the deformation of the guiding groove 41 is large, that is, the osteotomy guide tool 4 is deformed, and the operator can replace or perform other treatments on the deformed osteotomy guide tool 4 according to the actual situation. Further, if the offset is not greater than the expected value, and the operator can further choose whether to update the standard value as the pose parameter value of the open end of the guiding groove 41 actually obtained in step S1, so as to perform the surgical operation more accurately in the subsequent period.

Please refer to FIG. 8, in the second example of this embodiment, the detection end 101 of the detection element 100 includes a plunger whose width matches the width of the guiding groove 41 of the osteotomy guide block 40 of the osteotomy guide tool 4. The plunger is used to be inserted into the guiding groove 41. As shown in FIG. 7, the plunger has a width matching with the width of the guiding groove 41, the plunger has a height preferably not smaller than the depth of the guiding groove 41. In this configuration, the plunger can be inserted from the open end of one side of the guiding groove 41 is inserted and extend to the open end of the other side. The plunger forms a full coverage of the entire side wall of the guiding groove 41 in the height direction. In actual use, the step of acquiring the sliding information of the detection end 101 when the detection element 100 slides in the guiding groove 41 along the extending direction of the guiding groove 41 includes: acquiring a sliding information of the detection end 101 of the detection element 100 along the extending direction of each of the guiding grooves 41 to obtain a pose parameter of the inner surface of each of the guiding grooves 41. In practice, after inserting the plunger into the guiding groove 41, the plunger slowly moves from one end to the other end along the extending direction of the guiding groove 41. In this configuration, the two inner surfaces of one guiding groove 41 can be obtained in a single calibration. Other structures and principles of the example are similar to the first example of this embodiment, and reference may be made to the description of the first example of this embodiment. It should be noted that, if the plunger cannot be inserted into the guiding groove 41, it means that the guiding groove 41 has been deformed. The pose parameter of the feature portion of the osteotomy guide tool 4 in the coordinate system of the trackable element cannot be obtained. At this time, the offset between the pose parameter of the feature portion and the corresponding standard value can be directly determined to be greater than the expected value, and the osteotomy guide tool 4 is determined as deformed. In other examples, the detection end 101 of the detection element 100 includes more than two plungers. The distribution of more than two plungers is consistent with the distribution of the guiding grooves 41 of the osteotomy guide block 40, and all the guiding grooves 41 have the same length in the extending direction. In this way, all the plungers can be inserted into the corresponding guiding grooves 41 and slide at the same time, so that the pose parameters of more than two guiding grooves 41 can be obtained by single one slide. Referring to FIG. 9, in the third example of this embodiment, the detection end 101 of the detection element 100 includes a sheet portion, the length of the sheet portion matches with the length the guiding groove of the osteotomy guide block of the osteotomy guide tool. As shown in FIG. 9, the osteotomy guide block 40 includes three linear guiding groove 41, the three guiding grooves 41 have different lengths. Correspondingly, the lengths of the three sheet portions match with the lengths of the three guiding grooves 41, respectively. Optional, the detection end 101 of detection element 100 is detachably connected to the positioning target 102. With such a configuration, in a verification process, different sheet portions can be replaced according to the different guiding grooves 41 to be verified, and it is only necessary to perform once calibration to the detection target 100. It can be understood that in some other embodiments, the number of guiding grooves 41 is not limited to three, and the shape is not limited to a straight line, as long as the number and shape of the sheet portions correspond to the guiding groove 41. In actual use, after the sheet portion to be inserted is inserted into the guiding groove 41, the pose parameters of the guiding groove 41 can be obtained. In other examples, the detection end 101 of the detection element 100 includes more than two sheet portions, and the distribution of more than two sheet portions is consistent with the distribution of the guiding groove 41 of the osteotomy guide block 40, that is, all sheet portions can be inserted into the corresponding guiding grooves 41 at the same time, so as to obtain the pose parameters of more than two guiding grooves 41 at the same time. Other structures and principles of the example are similar to the first example of this embodiment, and reference may be made to the description of the first example of this embodiment.

Please refer to FIG. 10, in the fourth example of this embodiment, the detection end 101 of the detection element 100 includes a pin whose outer dimension matches with the inner dimension of the guiding hole 42 of the osteotomy guide block 40 of the osteotomy guide tool 4. As shown in FIG. 10, the guiding hole 42 is a round hole, and the pin is in a cylindrical shape. The outer diameter of the pin matches with the inner diameter of the guiding hole 42. The guiding hole 42 is a through hole and the pin has an axial length not smaller than the depth of the guiding hole 42. In this configuration, the pin can be inserted from the open end of one side of the guiding hole 42 and extend to the open end of the other side, and the pin forms an overall coverage to the entire guiding hole 42 in the axial direction. In actual use, after inserting the pin into the guiding hole 42, the pose parameter of the guiding hole 42 can be obtained. Optionally, the pin is detachably connected to the positioning target 102. In this configuration, when the osteotomy guide block 40 includes multiple guiding holes 42 of different specifications or both guiding holes 42 and guiding grooves 41 at the same time, the pins of different specifications can be removed and replaced by pins of different specifications, or by removing and replacing the pins and the sheet portion. In the verification process, the detection element 100 only needs to be calibrated once. In other example, the detection end 101 of the detection element 100 includes more than two pins, and the distribution of more than two pins is consistent with the distribution of the osteotomy guide block 40 of the guiding holes 42, that is, all pins can be simultaneously inserted into the corresponding guiding holes 42 to obtain the pose parameters of the more than two guiding holes 42 at the same time. Other structures and principles of the example are similar to the first example of this embodiment, and reference may be made to the description of the first example of this embodiment.

Please refer to FIG. 11 and FIG. 12, in the fifth example of this embodiment, the pins are triangular, and in the sixth example of this embodiment, the pins are rectangular. When the guiding hole 42 is circular, in addition to the cylindrical shape as described in the fourth example of this embodiment, the cross section of the pin can also be a polygon with a circumscribed circle whose diameter is the inner diameter of the guiding hole 42. The pin is not limited to a triangular prism shape or a quadrangular prism shape, but can also be other polygonal prisms, and the guiding hole 42 is not limited to a round hole, in some embodiments, the guiding hole 42 is designed with a shape that matches with the outer contour of the pin. For example, when the pin is triangular prism-shaped, the guiding hole 42 may be triangular or hexagonal, those skilled in the art can configure the pin and the guiding hole 42 according to the above descriptions. Same as the fourth example of this embodiment, the pins in the fifth example and the sixth example of this embodiment are also detachably connected with the positioning target 102.

Referring to FIG. 13, in a seventh example of this embodiment, the detection end 101 includes both a sheet portion and a pin, and the length of the sheet portion matches with the length of the guiding groove 41 of the osteotomy guide block 40 of the osteotomy guide tool 4, and the outer diameter of the pin matches with the inner diameter of the guiding hole 42 of the osteotomy guide block 40 of the osteotomy guide tool 4. As shown in FIG. 13, the osteotomy guide block 40 includes three linear guiding groove 41 and multiple guiding holes 42. Correspondingly, the detection end 101 includes three sheet portions and multiple pins at the same time, and the distribution of three sheet portions and multiple pins is consistent with the distribution of the guiding groove 41 and the guiding hole 42 of the osteotomy guide block 40. With this configuration, all sheet portions and pins can be inserted into the corresponding guiding groove 41 and guiding hole 42 at the same time, and the pose parameters of all the guiding groove 41 and guiding hole 42 can be obtained at once. Other structures and principles of the example are similar to the first example of this embodiment, and reference may be made to the description of the first example of this embodiment. It should also be noted that in the third example to the seventh example of this embodiment, if a sheet portion or any one of the pins cannot be inserted into the corresponding guiding groove 41 and the guiding hole 42, it means that the guiding groove 41 or the guiding hole 42 has been deformed. The pose parameter of the feature portion of the osteotomy guide tool 4 in the coordinate system of the trackable element cannot be obtained. At this time, the offset between the pose parameter of the feature portion and the corresponding standard value can be directly determined to be greater than the expected value, and the osteotomy guide tool 4 is determined as deformed.

In the second embodiment, the verification method of the osteotomy guide tool, the verification system and the detection element are provided. An offset is obtained by obtaining the pose parameters of the inner surface of the guiding groove 41 and/or the guiding hole 42 of the osteotomy guide block 40, and comparing the obtained pose parameters with the corresponding standard value. If the offset is greater than the expected value, the osteotomy guide tool 4 is determined as deformed. With this configuration, the guiding groove 41 and/or the guiding hole 42 of the osteotomy guide block 40 of the osteotomy guide tool 4 can be verified to avoid the deformation of the guiding groove 41 and/or the guiding hole 42 due to the repeated use or transportation of the osteotomy guide tool 4, thereby affecting its positioning accuracy and affects surgery.

Embodiment 3

Figure 14:
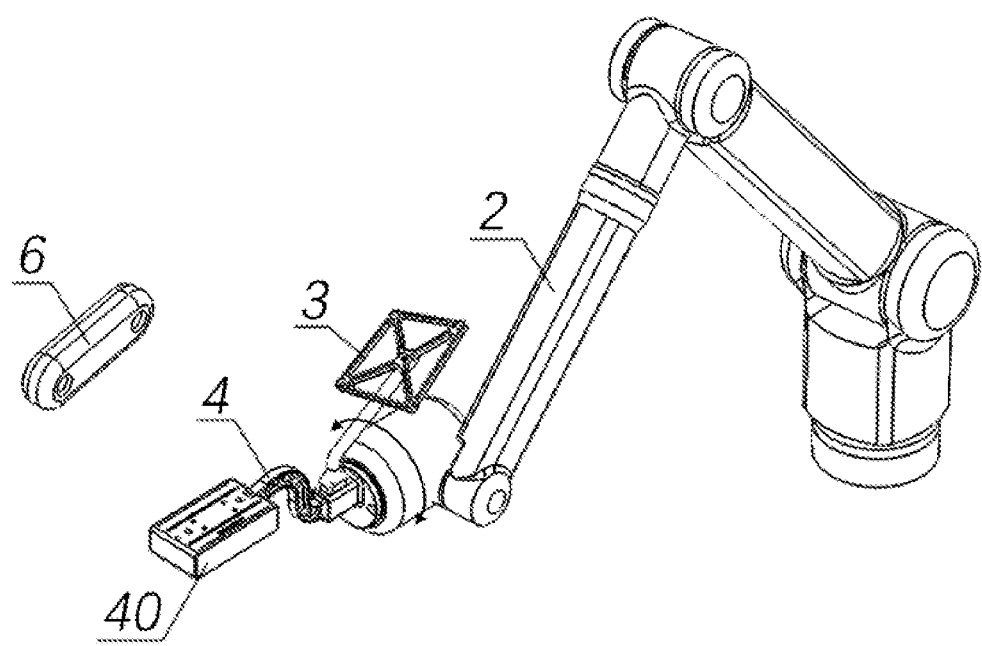
FIG. 14 is a structural schematic of a verification system for an osteotomy guide tool according to Embodiment 3 of the present disclosure.

Please refer to FIG. 14, which is a schematic diagram of a verification system for an osteotomy guide tool provided in Embodiment 3 of the present disclosure.

The verification method of the osteotomy guide tool, the verification system and the detection element provided by the third embodiment of the present disclosure are basically the same as the verification method of the osteotomy guide tool, the verification system and the detection element provided by the first embodiment. For the same part is not described, only the differences will be described below.

As shown in FIG. 14, the difference from the first embodiment is that in this embodiment, the verification system of the osteotomy guide tool only includes an osteotomy guide tool 4, a trackable element 3, a navigation device 6 and a control device, the verification system does not include the detection element 100. The osteotomy guide tool is arranged at the end of a robotic arm 2. The feature portion includes the geometric center point of the osteotomy guide block 40.

In this embodiment, the step S1 of the verification method of the osteotomy guide tool includes:

Step SC1: driving the osteotomy guide tool 4 by the robotic arm 2 to rotate around a preset geometric center point of the osteotomy guide block 40. The coordinates of the preset geometric center point in the coordinate system of the robotic arm can be determined by a three-coordinate calibration instrument at the factory or obtained from the design value of the osteotomy guide tool 4.

Step SC2: calculating a pose parameter of the geometric center point of the osteotomy guide block 40 in the coordinate system of the trackable element based on a point cloud information formed by the trackable element 3 connected to the osteotomy guide tool 4 during rotation. The control device can obtain the rotation trajectory of the tool target 3 (that is, the cloud information) by the navigation device 6. Through calculation, the position of the rotation center of the osteotomy guide tool 4 in the coordinate system of the trackable element can be further obtained, that is, the pose parameter of the geometric center point of the osteotomy guide block 40 in the coordinate system of the trackable element is calculated.

Further in the step S2, the obtained pose parameter of the geometric center point of the osteotomy guide block 40 of the osteotomy guide tool 4 is compared with the corresponding standard value (such as the pose parameters of the geometric center point of the osteotomy guide block 40 determined by the three-coordinate calibration instrument in the coordinate system of the trackable element) to obtain the offset between the pose parameter of the geometric center point of the osteotomy guide block 40 of the osteotomy guide tool 4 and the standard value. If the offset is greater than the expected value, the osteotomy guide tool 4 is determined as deformed. After the step of comparing between the offset and the expected value, further operations and methods are described as those in Embodiment 1, which will not be described in this embodiment.

Through the verification method of the osteotomy guide tool provided in this embodiment, the geometric center point of the osteotomy guide block 40 of the osteotomy guide tool 4 in the coordinate system of the robotic arm can be calculated by means of the movement trajectory, which can be verified by using the structure detected by the detection element 100 in another embodiment.

Optionally, in the step SC1, the connection points between the robotic arm 2 and the osteotomy guide tool 4 are taken as the movement points, the movement points each follows a circular movement around a movement center in a movement plane, wherein an angle between: i) a movement line defined by connecting any one of the movement points and the preset geometric center point and ii) a center line defined by connecting the movement center and the preset geometric center point is not smaller than 30°. For a further description, the movement mode of the robotic arm 2 driving the osteotomy guide tool 4 is abstracted. The connection point between the robotic arm 2 and the osteotomy guide tool 4 is taken as a movement point, and the trajectory of the movement point can actually be spherical around the preset geometric center point. In order to improve the accuracy of calculating the rotation center, the robotic arm 2 can be configured to drive the osteotomy guide tool 4 to rotate around a rotation axis passing through a preset geometric center point, and the movement point moves in a circular motion around a movement center on a movement plane. The movement plane is perpendicular to the rotation axis, and the movement center is arranged on the rotation axis. The movement line is defined by connecting the movement point and the preset geometric center point, and the center line is defined by connecting the movement center and the preset geometric center point, here, the angle between the limited movement line and the center line is not smaller than 30°. The accuracy of calculating the rotation center point can be improved. It can be understood that when the robotic arm 2 drives the osteotomy guide tool 4 to rotate around a rotation axis passing through the preset geometric center point, the movement point and the preset geometric center point actually appear as a cone. When the vertex angle of the cone is too small, the accuracy of the calculated rotation center is low.

It should be noted that the embodiments in this specification are described in a progressive manner. Each embodiment focuses on the differences from other embodiments. The same and similar parts between the embodiments can be referred to each other. In addition, the different parts between the various embodiments can also be used in combination with each other, which is not limited in the present disclosure.

In summary, the verification method of the osteotomy guide tool, the verification system and the detection element according to the present disclosure relate: first obtaining a pose parameter of a feature portion of an osteotomy guide tool in a coordinate system of a trackable element; then comparing the obtained pose parameter of the feature portion of the osteotomy guide tool with a corresponding standard value to obtain an offset between the pose parameter of the feature portion of the osteotomy guide tool and the standard value; if the offset is greater than an expected value, the osteotomy guide tool is determined as deformed. With this configuration, the osteotomy guide tool can be verified to avoid deformation of the osteotomy guide tool during repeated use or transportation, affecting its positioning accuracy and affecting the operation.

The above description is only a description of the embodiments of the present invention, and does not limit the scope of the present invention. Any changes or modifications made by those skilled in the art according to the above disclosure shall fall within the protection scope of the claims.

What is claimed is:

1. A verification system, comprising:
an osteotomy guide tool comprising an osteotomy guide block and a target mounting portion connected with the osteotomy guide block;
a detection element for verifying the osteotomy guide tool, comprising: a detection end for contacting a feature portion of the osteotomy guide tool; and a positioning target connected to the detection end and configured to provide a pose parameter of the feature portion of the osteotomy guide tool in a coordinate system of a trackable element;
the trackable element provided on the target mounting portion;
a navigation device configured to communicate with the trackable element and the detection element, thereby obtaining a pose parameter of the trackable element and the detection element by the positioning target; and
a control device in communication with the navigation device;
wherein the detection end of the detection element is configured to contact the feature portion of the osteotomy guide tool, andwherein the control device comprises a storage medium that includes instructions for determing whether the osteotomy guide tool is determined as deformed, when said instructions being executed by the control device, they obtain the pose parameter of the feature portion of the osteotomy guide tool in the coordinate system of the trackable element and compare the obtained pose parameter of the feature portion of the osteotomy guide tool with a corresponding standard value to obtain an offset between the pose parameter of the feature portion of the osteotomy guide tool and the standard value; and wherein if the offset between the obtained pose parameter and the corresponding standard value is greater than an expected value, the osteotomy guide tool is determined as deformed.

2. The verification system of claim 1, wherein the detection end of the detection element comprises a sharp portion for abutting the feature portion of the osteotomy guide tool.

3. The verification system of claim 2, wherein the feature portion comprises a guiding groove of an osteotomy guide block, and wherein a sharp tip of the sharp portion is able to extend into an open end of the guiding groove.

4. The verification system of claim 3, wherein the sharp portion is a cone, and wherein the size of an end of the sharp portion connected to the positioning target is larger than the size of the open end of the guiding groove.

5. The verification system of claim 4, wherein the navigation device is configured to obtain the pose parameter of the open end of the guiding groove by the positioning target.

6. The verification system of claim 1, wherein the detection end of the detection element comprises a plunger having a width matching with a width of a guiding groove of an osteotomy guide block of the osteotomy guide tool, and wherein the plunger is configured to be inserted into the guiding groove.

7. The verification system of claim 1, wherein the detection end of the detection element comprises a sheet portion having a length matching with a length of a guiding groove of an osteotomy guide block of the osteotomy guide tool and/or a pin having an outer dimension matching with an inner dimension of a guiding hole of the osteotomy guide block of the osteotomy guide tool.

8. The verification system of claim 1, wherein the detection end is detachably connected to the positioning target.

* * * * *